United States Patent [19]

Warriner

[11] Plant 5,040

[45] Apr. 19, 1983

[54] ROSE PLANT 74-1489-2

[75] Inventor: William A. Warriner, Tustin, Calif.

[73] Assignee: Jackson & Perkins Company, Medford, Oreg.

[21] Appl. No.: 318,969

[22] Filed: Nov. 6, 1981

[51] Int. Cl.[3] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having an upright plant habit with dark green, glossy foliage, red-tipped yellow buds, and fully double open flowers.

1 Drawing Figure

This present invention relates to a new and distinct variety of rose plant of the hybrid tea class which was originated by me by crossing the variety Precilla, U.S. Plant Pat. No. 3,726, with the variety Sunshine, U.S. Plant Pat. No. 3,791.

The primary objective of this breeding was to produce a new rose variety of a vigorous, prolific, upright plant producing yellow blooms of good color, form, and substance. This objective was substantially achieved along with other desirable improvements as evidenced by the following unique combination of characteristics which are outstanding in the new variety and which distinguish it from its parents as well as from all other varieties of which I am aware:

1. An upright plant habit, bearing dark green, glossy foliage.
2. Bud of a rich yellow color tipped with red.
3. Fully double (40 petals) open flowers fading only slightly upon aging.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Precilla, U.S. Plant Pat. No. 3,726.

*Pollen parent.*—Sunshine, U.S. Plant Pat. No. 3,791.

Classification:

*Botanical.*—Rosa hybrid.

*Commercial.*—Hybrid tea.

FLOWER

Observations made from specimens grown at Irvine, Calif. during August.

Blooming habit: Continuous.

Bud:

*Size.*—1 to 1¼ inches when petals start to unfurl.

*Form.*—Long, blunt top.

*Color.*—When sepals first divide, Yellow 10B; edges of petals Red 46A, some overlay of Red 46D on center of petals. When half blown, upper side of petals Yellow-Orange 16A; lower side of petals Yellow-Orange 16A.

*Sepals.*—Color: Outer surface Green 138A, smooth. Three appendaged sepals lightly appendaged with some glands on edges; two unappendaged sepals hairy edged.

*Receptacle.*—Color: Green 138A. Shape: Funnel. Size: Large. Surface: Smooth.

*Peduncle.*—Length: Short. Surface: Smooth. Color: Light green to bronzy green. Strength: Stiff, erect.

*Opening.*—Petals fold outward evenly.

Bloom:

*Size.*—Large. Average open size is 4½".

*Borne.*—Singly.

*Stems.*—Long to medium, strong.

*Form.*—When first open, high center. Permanence: Outer petal edges slightly curled.

*Petalage.*—Number of petals under normal conditions: 40.

*Color.*—Center of flower: Upper side of petals Yellow 11A; reverse side of petals Yellow 11A; base of petals Yellow 11A. General tonality from a distance, Yellow 11A.

*Variegations.*—Outer petal edges retain red pigment as in the bud.

*Discoloration.*—General tonality at end of first day, none; third day, lightens to Yellow 11C.

*Fragrance.*—None.

Petals:

*Texture.*—Thick, leathery.

*Shape.*—Obovate.

*Form.*—Tips slightly recurved.

*Arrangement.*—Imbricated. Petaloids in center, few.

*Persistence.*—Drop off cleanly.

*Lastingness.*—On the plant, long. As cut flower, long.

Reproductive parts:

*Anthers.*—Large. Color: Golden yellow. Arrangement: Regular around styles.

*Filaments.*—Color: Reddish.

*Pollen.*—Gold yellow.

*Styles.*—Color: White.

*Stigmas.*—Color: Red.

PLANT

Form: Bush.

Growth: Vigorous, upright.

Foliage: Number of leaflets on normal mid-stem leaves: 5 or 7.

*Size.*—Large.

*Quantity.*—Normal.

*Color.*—New foliage: Dark green but showing coloration of anthocyanin pigment. Old foliage: Dark green.

Leaflets:

*Shape.*—Oval pointed.

*Texture.*—Upper side: glossy.

*Edge.*—Serrated.

*Serration.*—Single, small.

*Petiole.*—Rachis: Color: Reddish. Underside: Prickles.

*Stipules.*—Long.

*Disease resistance.*—Mildly resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, many. On laterals from stalk, many.

*Form.*—Narrow base, long, hooked downward.

*Color when young.*—Brown.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its upright plant habit, glossy foliage, red tipped yellow buds, and lighter yellow open flowers.

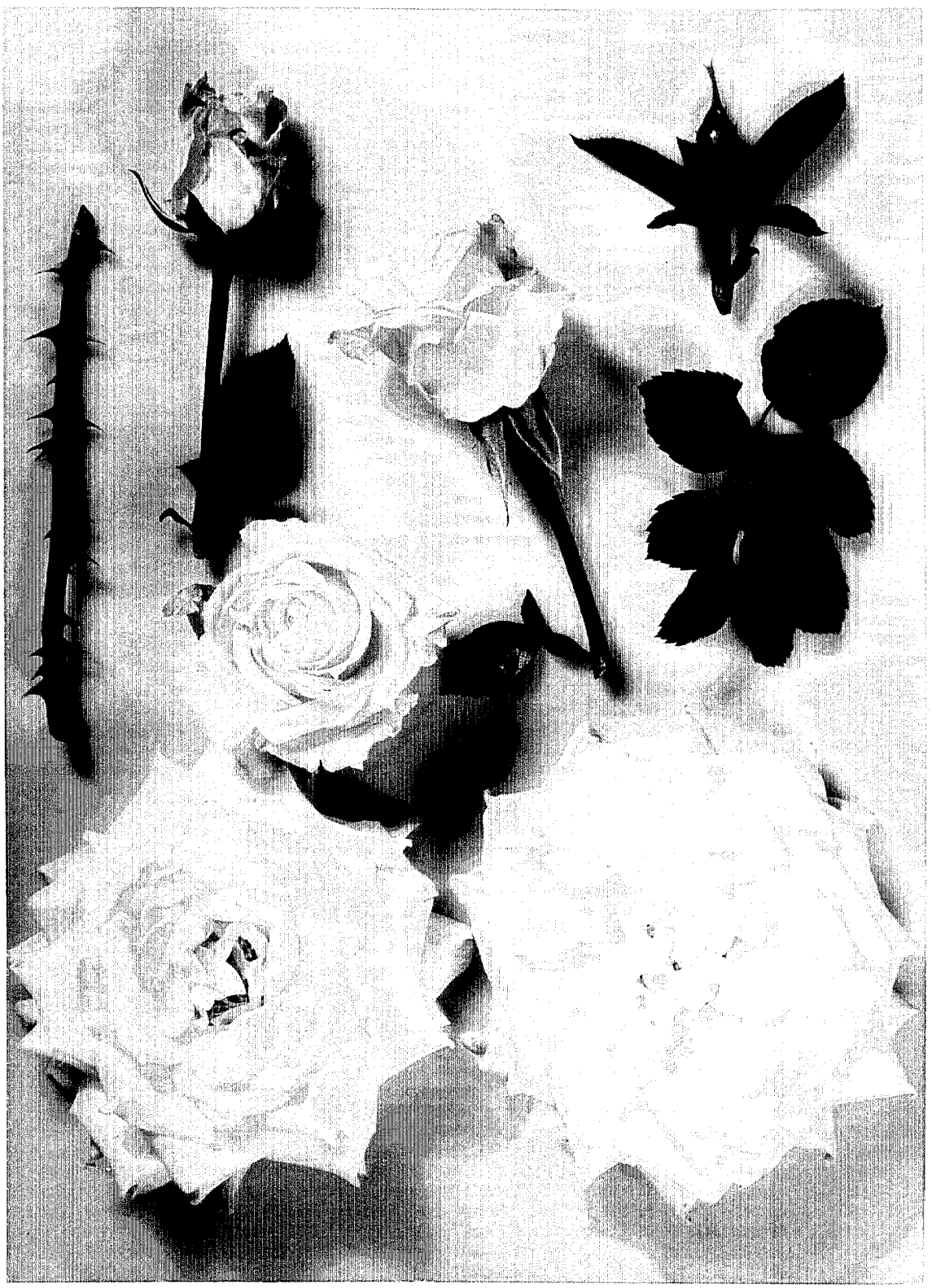

* * * * *